United States Patent
Xiao et al.

(10) Patent No.: US 11,529,248 B2
(45) Date of Patent: Dec. 20, 2022

(54) BRANCH VESSEL STENT

(71) Applicant: Lifetech Scientific (Shenzhen) Co., Ltd., Shenzhen (CN)

(72) Inventors: Benhao Xiao, Shenzhen (CN); Yi Fang, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 172 days.

(21) Appl. No.: 16/913,764

(22) Filed: Jun. 26, 2020

(65) Prior Publication Data
US 2020/0330248 A1    Oct. 22, 2020

Related U.S. Application Data

(63) Continuation of application No. PCT/CN2018/121720, filed on Dec. 18, 2018.

(51) Int. Cl.
*A61F 2/852* (2013.01)
*A61F 2/915* (2013.01)

(52) U.S. Cl.
CPC .... *A61F 2/852* (2013.01); *A61F 2002/91575* (2013.01); *A61F 2210/0076* (2013.01)

(58) Field of Classification Search
CPC .. A61F 2/852; A61F 2002/91575; A61F 2/07; A61F 2/89; A61F 2/90; A61F 2/064;
(Continued)

(56) References Cited

U.S. PATENT DOCUMENTS 5,639,278 A * 6/1997 Dereume .................. A61F 2/07
                                                          623/1.13
5,741,327 A * 4/1998 Frantzen ................... A61F 2/91
                                                          606/198
(Continued)

FOREIGN PATENT DOCUMENTS

CN    102451051 A    5/2012
CN    103298428 A    9/2013
(Continued)

OTHER PUBLICATIONS

Office Action dated Jul. 2, 2021 for corresponding India Application No. 202017029131.
(Continued)

*Primary Examiner* — Paul B Prebilic
(74) *Attorney, Agent, or Firm* — Raymond Sun

(57) ABSTRACT

A branch vessel stent comprising a stent body and a first developing member, wherein the first developing member comprises a first developing portion and a second developing portion. A length of the first developing portion and a length of the second developing portion in an axial direction of the stent body are both not less than 0.5 mm. A distance between the intersections of the first developing portion and the second developing portion on a plane perpendicular to the axial direction of the stent body gradually increases from a position where the distance is the minimum distance to an end that is away from a first end of the first developing portion or the second developing portion. The minimum distance between the intersections of the first developing portion and the second developing portion on a plane perpendicular to the axial direction of the stent body is not more than 2 mm. The branch vessel stent is capable of accurately positioning the position thereof, and is capable of
(Continued)

identifying a distortion and knotting of the stent for the branch vessel.

2 Claims, 5 Drawing Sheets

(58) Field of Classification Search
CPC ........ A61F 2002/072; A61F 2210/0076; A61F 2230/0054; A61F 2230/0056; A61F 2250/0026; A61F 2250/0028; A61F 2250/0032; A61F 2250/0039; A61F 2250/0096; A61F 2250/0098
See application file for complete search history.

(56) References Cited

U.S. PATENT DOCUMENTS

| | | | | |
|---|---|---|---|---|
| 5,893,887 | A * | 4/1999 | Jayaraman | A61F 2/915 623/1.15 |
| 6,165,213 | A * | 12/2000 | Goicoechea | A61F 2/852 623/1.34 |
| 6,174,329 | B1 * | 1/2001 | Callol | A61F 2/91 606/198 |
| 7,291,167 | B2 * | 11/2007 | DiCaprio | A61F 2/91 623/1.34 |
| 7,338,519 | B2 * | 3/2008 | Fischell | A61F 2/915 623/1.15 |
| 7,794,493 | B2 * | 9/2010 | Burgermeister | A61L 31/022 623/1.34 |
| 7,988,720 | B2 * | 8/2011 | Brown | A61F 2/91 623/1.15 |
| 9,622,753 | B2 * | 4/2017 | Cox | A61B 17/12113 |
| 10,993,821 | B2 * | 5/2021 | Fang | A61F 2/852 |
| 2001/0016766 | A1 * | 8/2001 | Vardi | A61F 2/82 623/1.11 |
| 2006/0206202 | A1 * | 9/2006 | Bonhoeffer | A61F 2/2436 623/2.14 |
| 2006/0259123 | A1 * | 11/2006 | Dorn | A61F 2/95 623/1.13 |
| 2012/0035714 | A1 * | 2/2012 | Ducke | A61F 2/07 623/1.34 |
| 2012/0130478 | A1 * | 5/2012 | Shaw | A61F 2/07 623/1.35 |
| 2018/0333251 | A1 * | 11/2018 | Zigelboim | A61F 2/962 |
| 2019/0015227 | A1 * | 1/2019 | Xiao | A61F 2/86 |
| 2019/0167455 | A1 * | 6/2019 | Myung | A61F 2/848 |
| 2020/0330248 | A1 * | 10/2020 | Xiao | A61F 2/852 |
| 2022/0160526 | A1 * | 5/2022 | Chun | A61F 2/07 |

FOREIGN PATENT DOCUMENTS

| | | | |
|---|---|---|---|
| CN | 103298428 A | 9/2013 | |
| CN | 104586536 A | 5/2015 | |
| EP | 3075352 A1 * | 10/2016 | A61F 2/07 |

OTHER PUBLICATIONS

International Search Report dated Mar. 18, 2019 for corresponding PCT Application No. PCT/CN2018/121720.
CN 101836911 A (Microport Medical Shanghai Co., Ltd.) Sep. 22, 2010 (Sep. 22, 2010) description, paragraph [0059], and figure 5.
Office Action for corresponding EP Application No. 18 893 638.9.
Office Action for corresponding EP Application No. 18 893 638.9 dated 2021.

* cited by examiner

BRANCH VESSEL STENT

FIELD

The embodiments relate to the field of medical apparatuses and instruments, and in particular, to a branch vessel stent.

BACKGROUND

In case of vascular occlusion caused by a lesion, a vascular stent is usually implanted into the lesion area by balloon dilatation of lumen, so as to achieve the purposes of supporting the blood vessel in regions experiencing vascular occlusion and stenosis, reducing elastic retraction, and reshaping the blood vessel and maintaining the smooth blood flow in the lumen. However, when a lesion occurs nearby a branch vessel, the vascular lesion is treated by a main body stent, which may block the blood flow of the branch vessel, resulting in occlusion or insufficient blood supply to the branch vessel.

Referring to FIG. 1, a diseased blood vessel 10 includes a main vessel 110 and a branch vessel 120. The branch vessel 120 stretches out from the main vessel 110, and the branch vessel 120 is connected with the main vessel 110 to form an intersection 111, and a lesion 112 is formed on the vascular wall of the main vessel 110 which is near the intersection 111. Referring together to FIG. 2, a conventional method is to implant a main body stent 200 into the main vessel 110 while reconstructing the diseased blood vessel 10, and to perform in-situ fenestration at the intersection 110 where the main body stent 200 is located, and then to introduce a stent for the branch vessel via a branch guide wire, and finally to complete the reconstruction of the branch vessel.

However, this method fails to properly account for the relative position of the branch vessel to the main body stent during the in-situ fenestration, so that it is difficult to control the extent to which the branch vessel stent extends into the lumen of the main body stent. When the branch vessel stent extends too far into the main body stent, it may result in the obstruction of blood flow in the main body stent, and when the branch vessel stent extends for an insufficient distance into the main body stent, it may result in poor anchorage of the branch vessel stent in the main body stent. Moreover, a distal end of the branch vessel stent may also block a port of distal branch vessel. In addition, it is difficult to identify the distortion or knotting of the branch vessel based upon the reconstruction mode thereof.

SUMMARY

Based on the above, it is necessary to provide a stent for a branch vessel in view of the problems that the prior art fails to indicate the position of the branch vessel entering into the main body stent during the reconstruction of the branch vessel, and fails to identify the distortion or knotting of the branch vessel.

A branch vessel stent includes a stent body and a first developing member; the stent body is provided with a first end and a second end opposite to the first end; the first developing member is located between the first end and the second end as well as close to the first end, and the first developing member includes a first developing portion and a second developing portion.

The first developing portion extends along a first direction, and the second developing portion extends along a second direction; the first direction obliquely intersects with the second direction, moreover, the length of the first developing portion and the length of the second developing portion in an axial direction of the stent body are both not less than 0.5 mm.

The distance between the intersections of the first developing portion and the second developing portion on a plane perpendicular to the axial direction of the stent body gradually increases from a position where the distance is the minimum distance to an end that is away from the first end of the first developing portion or the second developing portion. The minimum distance between the intersections of the first developing portion and the second developing portion on a plane perpendicular to the axial direction of the stent body is not greater than 2 mm.

In one of the embodiments, the distance between the intersections of the first developing portion and an end that is close to the first end of the second developing portion on a plane perpendicular to the axial direction of the stent body is the minimum distance.

In one of the embodiments, the stent body includes a bare stent and a coating film arranged on the bare stent; the first developing portion and the second developing portion are both arranged on the bare stent.

In one of the embodiments, the bare stent includes a plurality of axially arranged wave rings, the wave rings include a plurality of alternately arranged wave crests and wave troughs, and the adjacent wave crests are connected with the wave troughs through a wave rod; the first developing portion is arranged on the wave rod, and the second developing portion is arranged on a wave rod adjacent to the wave rod of a same wave ring where the first developing portion is located on.

In one of the embodiments, the length of the first developing portion and the length of the second developing portion are both ½ to ⅔ of that of the corresponding wave rods.

In one of the embodiments, an axial distance from the position where the distance between the intersections of the first developing portion and the second developing portion on the plane perpendicular to the axial direction of the stent body is the minimum distance, to the first end ranges from 5 mm-10 mm.

In one of the embodiments, the stent body includes a proximal portion, a connecting portion and a distal portion connected in succession; the first end is formed on one end that is away from the connecting portion of the proximal portion; a second end is formed on one end that is away from the connecting portion of the distal portion;

The cross-sectional area of one end that is close to the proximal portion of the connecting portion is smaller than or equal to that of one end that is close to the distal portion of the connecting portion; and an included angle which ranges from 0-30° is formed between the axial direction and a connecting line between the end that is close to the proximal portion of the connecting portion and the end that is close to the distal portion of the connecting portion; and the first developing member is arranged on the proximal portion.

One of the embodiments further includes a second developing member and a third developing member; the second developing member is arranged on the first end, and the developing member is arranged on the second end.

One of the embodiments further includes a skirt-sided stent surrounding the stent body, and the skirt-sided stent is connected with the stent body and extends towards the first end; and one end that is away from the first end of the first developing portion and one end that is away from the first end of the second developing portion are located at a joint portion of the skirt-sided stent and the stent body.

In one of the embodiments, the skirt-sided stent includes a flexible section and a folding section connected with the flexible section; and the flexible section is connected with the stent body; the distance from one end that is away from the first end of the first developing portion or the second developing portion, to the position where the distance between the intersections of the first developing portion and the second developing portion on the plane perpendicular to the axial direction of the stent body is the minimum distance, is equal to the length of a contour line of the flexible section.

A first developing member is arranged between a first end and a second end of the above branch vessel stent to conveniently observe the condition of the center of the branch vessel stent, which achieves the identification of any distortion and folding of the branch vessel stent during the release process. The distance between the intersections of the first developing portion and the second developing portion on a plane perpendicular to the axial direction of the stent body gradually increases from a position where the distance is the minimum distance to an end that is away from a first end of the first developing portion or the second developing portion. Therefore, during operation, the configuration may prevent developing members of the branch vessel stent from being tangled by the developing of wires in the stent body, moreover, it is beneficial to observe and pre-judge the relative position of the branch vessel stent in the main body stent while pulling the branch vessel stent.

DETAILED DESCRIPTION OF THE INVENTION

To make the above objectives, features and advantages of the more apparent, detailed embodiments will be described in detail with reference to the accompanying drawings hereafter. In the following description, numerous specific details are set forth to make full sense of the embodiments. The disclosure may be implemented in many other different modes, and those of ordinary skill in the art may make similar improvements within the spirit and scope of the disclosure, therefore, the embodiments are beyond the detailed embodiments disclosed hereafter.

It can be noted that when a member is referred to as being "fixed" to another member, it may be directly fixed on another member or an intervening member may be present. When a member is referred to as being "connected" to another member, it may be directly connected to another member or intervening members may be present. The terms used in the article, e.g., "vertical", "horizontal", "left", "right" serve illustrative purposes only, but are not intended to be the only embodiment.

Unless defined otherwise, all technical and scientific terms used herein have the same meaning as commonly understood by one of ordinary skill in the art. The terms used herein in the description are for the purpose of describing particular embodiments only and not intended to be limiting. The various features of the above-mentioned embodiments may be combined in any way, and in order to simplify the description, not all possible combinations of the features of the above-mentioned embodiments are described. However, as long as there is no conflict between these features, they should be considered to be within the scope of the description.

Figure 1:
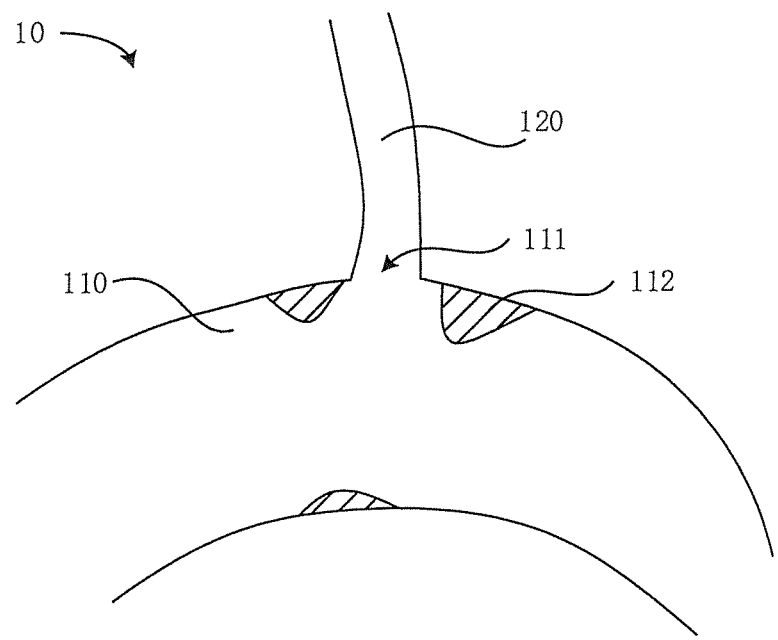
FIG. 1 is a schematic diagram showing a structure of a diseased blood vessel in one embodiment.
Figure 2:
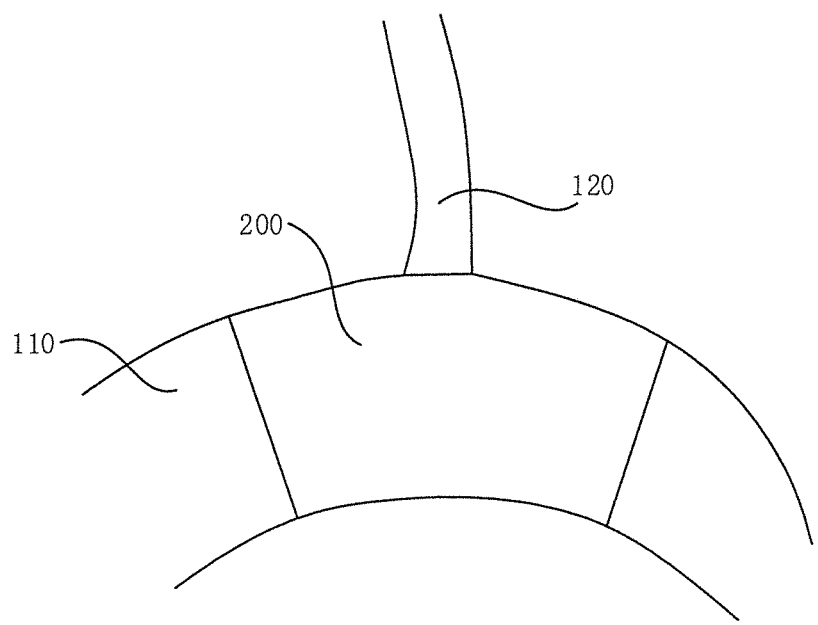
FIG. 2 is a schematic diagram showing a structure of the diseased blood vessel as shown in FIG. 1 implanted with a main body stent.
Figure 3:
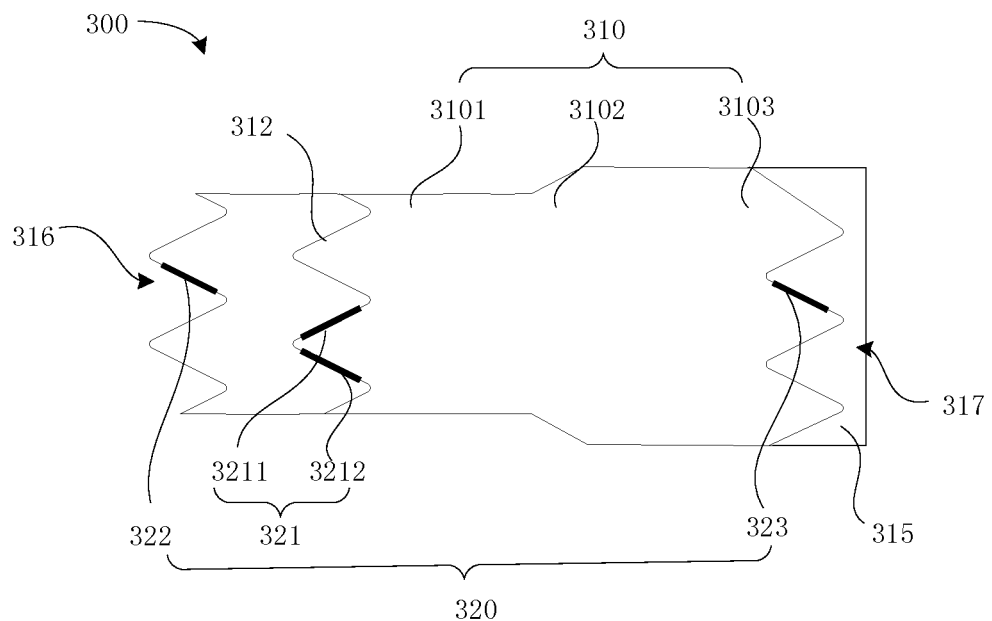
FIG. 3 is a schematic diagram showing a structure of a branch vessel stent in one embodiment.

Referring to FIG. 3, a branch vessel stent 300 of an embodiment includes a stent body 310 and a developing assembly 320; the developing assembly 320 is arranged on the stent body 310, and the stent body 310 is provided with a first end 316 and a second end 317 opposite to the first end.

For example, the stent body 310 includes a bare stent and a coating film 315 arranged on the bare stent. The bare stent includes a plurality of axially arranged wave rings 312. The wave ring 312 includes a plurality of alternately arranged wave crests and wave troughs, and adjacent wave crests and wave troughs are connected by a wave rod. In one of the embodiments, an included angle formed by extension lines of adjacent two wave rods ranges from 30°-120°.

In embodiments of the accompany drawings, the stent body 310 is formed with a proximal portion 3101, a connecting portion 3102, and a distal portion 3103 connected successively. A first end 316 is formed on an end that is opposite from the connecting portion 3102 of the proximal end 3101, and a second end 317 is formed on an end that is opposite from the connecting portion 3102 of the distal portion 3103. A coating film of the first end 316 forms a petal-shaped structure, so that blood passes through the first end conveniently; a coating film of the second end 317 is a flush structure.

In one of the embodiments, the cross-sectional area of the proximal portion 3101 is less than that of the distal portion 3103. The cross-sectional area of one end that is close to the proximal portion 3101 of the connecting portion 3102 is smaller than or equal to that of one end that is close to the distal portion 3103 of the connecting portion 3102; and an included angle which ranges from 0-30° is formed between an axial direction and a connecting line between the end that is close to the proximal portion 3101 of the connecting portion 3102 and the end that is close to the distal portion 3103 of the connecting portion 3102. Further, an included angle which ranges from 15°-20° is formed between the axial direction and a connecting line between the end that is close to the proximal portion 3101 of the connecting portion 3102 and the end that is close to the distal portion 3103 of the connecting portion 3102. The above structure enables the stent body 310 to form a tapered structure, which may enhance the anchoring force of the distal portion 3103, and meanwhile inhibit the transmission of aortic pulsation to the distal portion 3103 of a branch vessel stent. It can be appreciated that the proximal portion 3101, the connecting portion 3102 and the distal portion 3103 are differentiated for illustration only, which is not intended to indicate that the stent body 310 is separated on the connecting boundary; the stent body 310 may be an even integral structure.

The developing assembly 320 includes a first developing member 321, a second developing member 322, and a third developing member 323. The first developing member 321 is located between the first end 316 and the second end 317, and proximate to the first end 316. For example, the first developing member 321 is located on the proximal portion 3101. The second developing member 322 is arranged at the first end 316 and the third developing member 323 is arranged at the second end 317. The second developing member 322 serves to designate an initial end of the branch vessel stent 300. The third developing member 323 serves to another initial end of the branch vessel stent 300.

In embodiments of the accompany drawings, the developing assembly 320 is disposed on a bare stent of the stent body 310. It can be appreciated that in other embodiments, at least one developing member in the developing assembly 320 may also be formed on the coating film 315.

Referring continuously to FIG. 3, the first developing member 321 includes a first developing portion 3211 and a second developing portion 3212; the first development portion 3211 extends in a first direction, and the second developing portion 3212 extends in a second direction, and the first direction obliquely intersects with the second direction; and a length of first developing portion 3211 and a length of the second developing portion 3212 in the axial direction of the stent body 310 are not less than 0.5 mm. A distance between the intersections of the first developing portion 3211 and the second developing portion 3212 on a plane perpendicular to the axial direction of the stent body 310 gradually increases from a position where the distance is the minimum distance to an end that is away from the first end of the first developing portion 3211 or the second developing portion 3212. The minimum distance between the intersections of the first developing portion 3211 and the second developing portion 3212 on a plane perpendicular to the axial direction of the stent body 310 is not greater than 2 mm.

For example, a distance between the intersections of one end that is close to the first end 316 of the first developing portion 3211 and the second developing portion 3212 on a plane perpendicular to an axial direction of the stent body 310 is the minimum distance. In the present embodiment, the first developing portion 3211 and the second developing portion 3212 are symmetrical with each other along the axis of stent body 310.

It can be noted that the position where the distance between the intersections of the first developing portion 3211 and the second developing portion 3212 on the plane perpendicular to the axial direction of the stent body 310 is the minimum distance may be also located at the middle part of the first developing portion 3211 and/or the second developing portion 3212.

The first developing portion 3211 and the second developing portion 3212 are arranged on the bare stent. In embodiments of the accompany drawings, the first developing portion 3211 is arranged on a wave rod of the wave rings 312, and the second developing portion 3212 is arranged on a wave rod of the wave rings 312 adjacent to the first developing portion 3211. The first developing portion 3211 and the second developing portion 3212 are respectively formed by winding developing materials on corresponding wave rods respectively (e.g. tantalum wire, etc.).

Further, the length of the first developing portion 3211 and the length of the second developing portion 3212 are ½ to ⅔ of that of the corresponding wave rods, which is convenient for sheathing. For example, the first developing portion 3211 and the second developing portion 3212 extend towards the wave troughs from a position close to the wave crests, and the first developing portion 3211 and the second developing portion 3212 are not connected at wave crests. That is, the first developing portion 3211 and the second developing portion 3212 form a "\ /"-shaped structure with a gap between end points. In the present embodiment, the length of the first developing portion 3211 and the length of the second developing portion 3212 are both in the range of 2-4 mm.

It can be understood that in other embodiments, the first developing portion 3211 and the second developing portion 3212 may also be connected with each other, thus forming a V-shaped structure.

Referring to FIG. 3, the distance from a position where the distance between the intersections of the first developing portion 3211 and the second developing portion 3212 on the plane perpendicular to the axial direction of the stent body is the minimum distance, to the first end, ranges from 5 mm-10 mm, so that the length of one end of the branch vessel stent 300 for the branch vessel beyond a main body stent 200 ranges from 5-10 mm. Such a configuration can prevent the branch vessel stent 300 from falling off from the main body stent 200, and may decrease the influence of the branch vessel stent 300 on the blood flow in the main body stent 200.

The second developing member 322 and the third developing member 323 are also arranged on wave rods of the wave rings. The second developing member 322 is disposed on a first wave ring near the first end 316, and the third developing member 323 is disposed on a first wave ring near the second end 317. Both the second developing member 322 and the third developing member 323 may be formed by winding developing materials on wave rods. In the present embodiment, both the second developing member 322 and the third developing member 323 are I-shaped structures. The length of the second developing member 322 and the length of the third developing member 323 may both be ½ to ⅔ of that of the corresponding wave rods. In the present embodiment, the length of the second developing member 322 and the length of the third developing member 323 are both in a range of 2-4 mm.

It can be noted that the second developing member 322 and the third developing member 323 may be other structures, and the number thereof may be plural.

Figure 4:
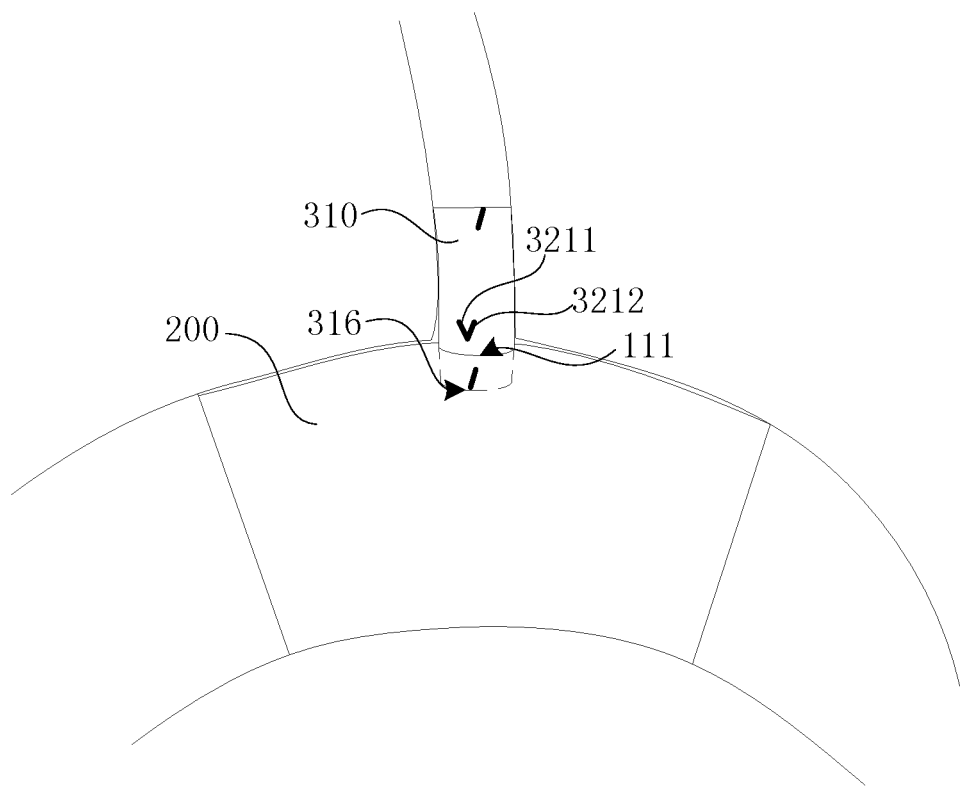
FIG. 4 is a schematic diagram showing a structure of the branch vessel stent as shown in FIG. 3 implanted into the main body stent.

Referring together to FIG. 4, when the branch vessel stent 300 is used for vascular reconstruction, the main body stent 200 is first completely released at a lesion, and then an in-situ fenestration is conducted to expand to the preset pore diameter via a fenestration instrument at a position where the main body stent 200 is located at an intersection 111 of the branch vessel; and then the branch vessel stent 300 is fed via a lumen of a sheath along a path of the branch guide wire. During the implantation of the branch vessel stent 300, the first end 316 is a front end of the branch vessel stent 300 for moving; the branch vessel stent 300 is implanted until one end close to the first end 316 of the first developing portion 3211 or the second developing portion 3212 completely enters into the main body stent 200, finishing the initial positioning at this time; then it starts to release the branch vessel stent 300 from the lumen of the sheath until one end away from the first end 316 of the first developing portion 3211 or the second developing portion 3212 is just released;

afterwards, a release device of the lumen of the sheath is locked, and the lumen of the sheath and the branch vessel stent 300 are pulled to move towards one end away from the main vessel of the branch vessel therein until the first developing portion 3211 and the second developing portion 3212 are flush with the wall of the intersection 111 at the position where the distance between the intersections thereof on the plane perpendicular to the axial direction the stent body 310 is the minimum distance, and the pulling is stopped at this time. Moreover, the branch vessel stent 300 is completely released from the lumen of the sheath, thus achieving the reconstruction of the branch vessel.

A first developing member 321 is arranged between the first end 316 and the second end 317 of the above branch vessel stent 300, which is convenient for observing the condition of the center of the branch vessel stent 300, and may be used for identifying the distortion and folding of the branch vessel stent 300 during the release process, as well as for positioning a length of the branch vessel stent 300 extending into the main body stent 200; moreover, the distance between the intersections of the first developing portion 3211 and the second developing portion 3212 on a plane perpendicular to the axial direction of the stent body 310 gradually increases from a position where the distance is the minimum distance to an end that is away from the first end of the first developing portion 3211 or the second developing portion 3212. During operation, when the first developing portion 3211 and the second developing portion 3212 are moved from the main body stent 200, so as to prevent developing members of the branch vessel stent 300 from being tangled by the developing of wires in the main body stent 200, and through the gradual change of the first developing member 321, it is beneficial to observe and pre-judge the relative position of the branch vessel stent 300 in the main body stent 200 during the pulling process, so as to achieve accurate positioning.

Figure 5:
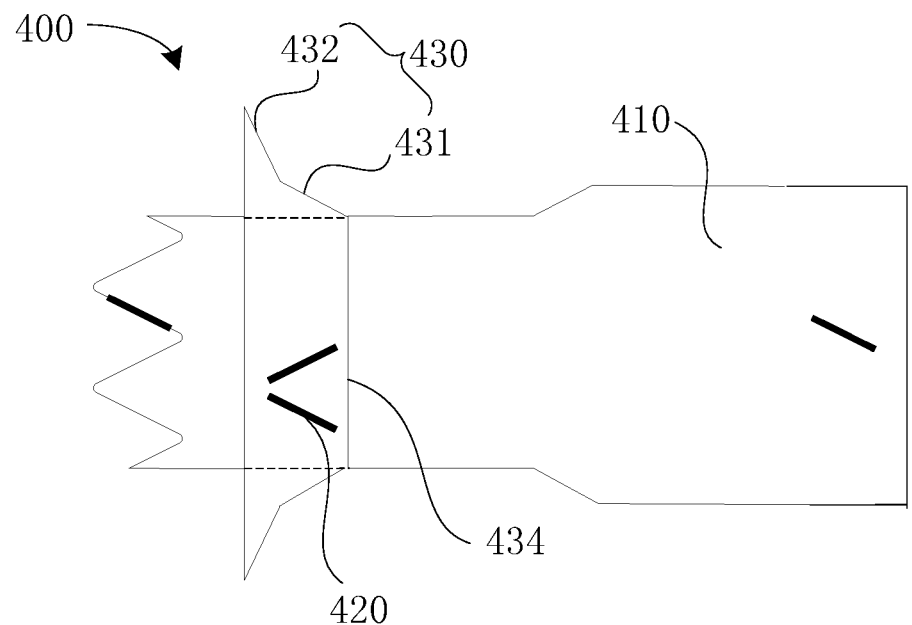
FIG. 5 is a schematic diagram showing a structure of the branch vessel stent under the natural state in another embodiment.

Referring to FIG. 5, a branch vessel stent 400 in another embodiment includes a stent body 410, a developing member 420 and a skirt-sided stent 430.

In embodiments of the accompany drawings, structures of the stent body 410 and the developing member 420 are substantially the same as those in the previous embodiments, and will not be described in detail herein.

In embodiments of the accompany drawings, the skirt-sided stent 430 surrounds the outside the stent body 410, and one end of the skirt-sided stent 430 is connected with the stent body 410, and another end of the skirt-sided stent 430 forms an open end towards the first end 416.

Figure 6:
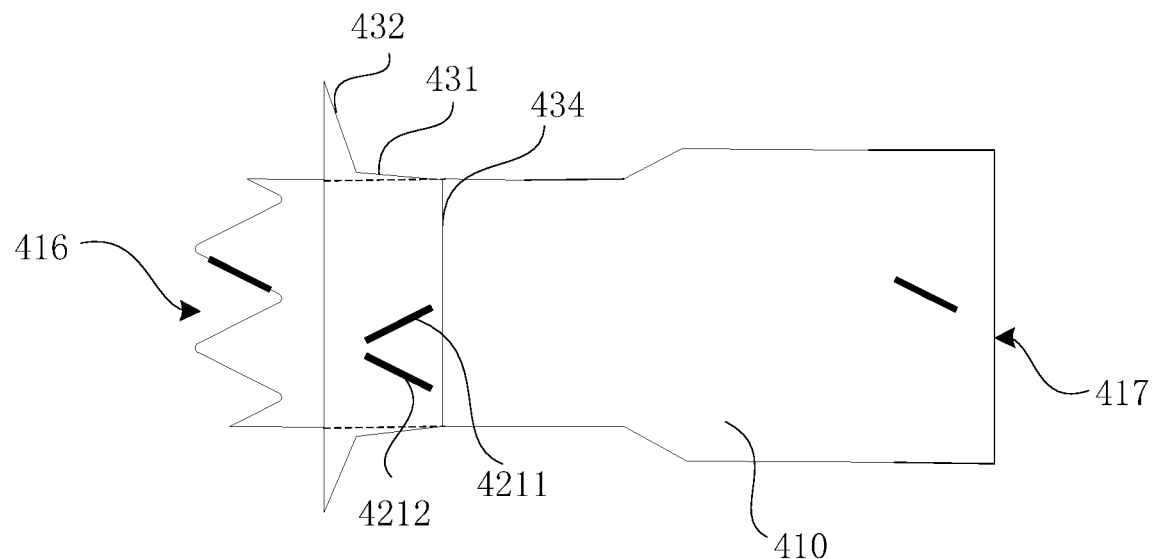
FIG. 6 is a schematic diagram showing a structure of the branch vessel stent as shown in FIG. 5 during sheathing.

Referring continuously to FIG. 5, the skirt-sided stent 430 includes a flexible section 431 and a folding section 432 connected with the flexible section 431. The flexible section 431 is connected with the stent body 410 via a connecting belt 434, and the connecting belt 434 is used for connecting and supporting the stent body 410 and the flexible section 431. Moreover, the connecting belt 434 may be formed by sewing, winding, cutting or coating. Referring to FIG. 6, one end that is away from the first end 416 of the first developing portion 4211 and the second developing portion 4212 is located at a joint portion of the skirt-sided stent 430 and the stent body 410, i.e., one end that is away from the first end 416 of the first developing portion 4211 and the second developing portion 4212 is flush with the connecting belt 434.

In embodiments of the accompany drawings, the folding section 432 is pivotally connected with one that is away from the connecting belt 434 of the flexible section 431, so that the folding section 432 may be gathered up or folded.

Further, the distance from one end that is away from the first end 416 of the first developing portion 4211 or the second developing portion 4212, to the position where the distance between the intersections of the first developing portion 4211 and the second developing portion 4212 on the plane perpendicular to the axial direction of stent body 410 is the minimum distance, is equal to the length of the contour line of the flexible section 431; that is, after insertion into the lumen of the sheath, the first developing portion 4211 and the second developing portion 4212 are flush with one end that is away from the stent body 410 of the flexible section 431 at the position where the distance between the intersections of the first developing portion 4211 and the second developing portion 4212 on the plane perpendicular to the axial direction of stent body 410 is the minimum distance, so as to indicate the initial position of the flexible section 431 via the first developing portion 4211 and the second developing portion 4212. In the present embodiment, when one end that is away from the connecting band 434 of the flexible section 431 extends toward the direction near the first end 416 to be abutted against the stent body 410, one end that is close to the first end 416 of the flexible section 431 is flush with one end that is close to the first end 416 of the first developing portion 4211 or the second developing portion 4212.

In one of the embodiments, when the skirt-sided stent 430 expands to a maximum position, the diameter of the end that is away from the flexible section 431 of the folding section 432 (i.e., the distance of the projection of the end that is away from the flexible section 431 of the folding section 431 on a plane perpendicular to the stent body 410) is 1.5 to 3 times the diameter of the stent body 410 located therein. The diameter of the skirt-sided stent 430 is larger than that of the stent body 410 where the skirt-sided stent 430 is located, and such a design can effectively reduce the risk of internal leakage caused by the cooperation between stents. For example, the length of the folding section 432 is less than that of the flexible section 431.

Figure 7:
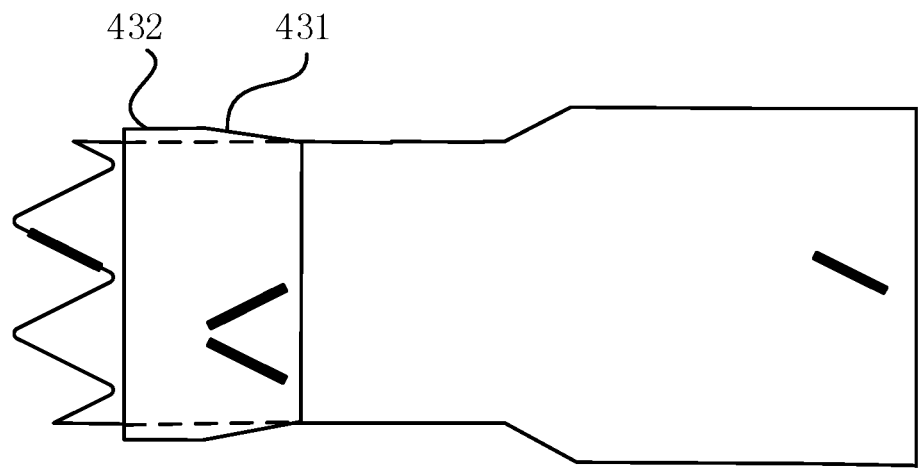
FIG. 7 is a schematic diagram showing a structure of the branch vessel stent as shown in FIG. 5 at the end of sheathing.

Referring together to FIGS. 5-7, in a natural state, the flexible section 431 of the branch vessel stent 400 is unfolded and the folding section 432 is turned over towards the direction away from the stent body 410, so as the skirt-sided stent 430 is turned over. When the branch vessel stent 400 enters the lumen of a sheath in the natural state, the second end 417 of the stent body 410 first enters the lumen until the connecting belt 434 enters therein; when pushed by the inner wall of the lumen, the flexible section 431 collapses against the stent body 410, and at that moment, the folding section 432 is still in an unfolded state. As the pushing continues, when pushed by the inner wall of the lumen, the folding section 432 collapses against the stent body 410, thus achieving the state shown in FIG. 7, thereby completing the sheathing process of the branch vessel stent.

Figure 8:
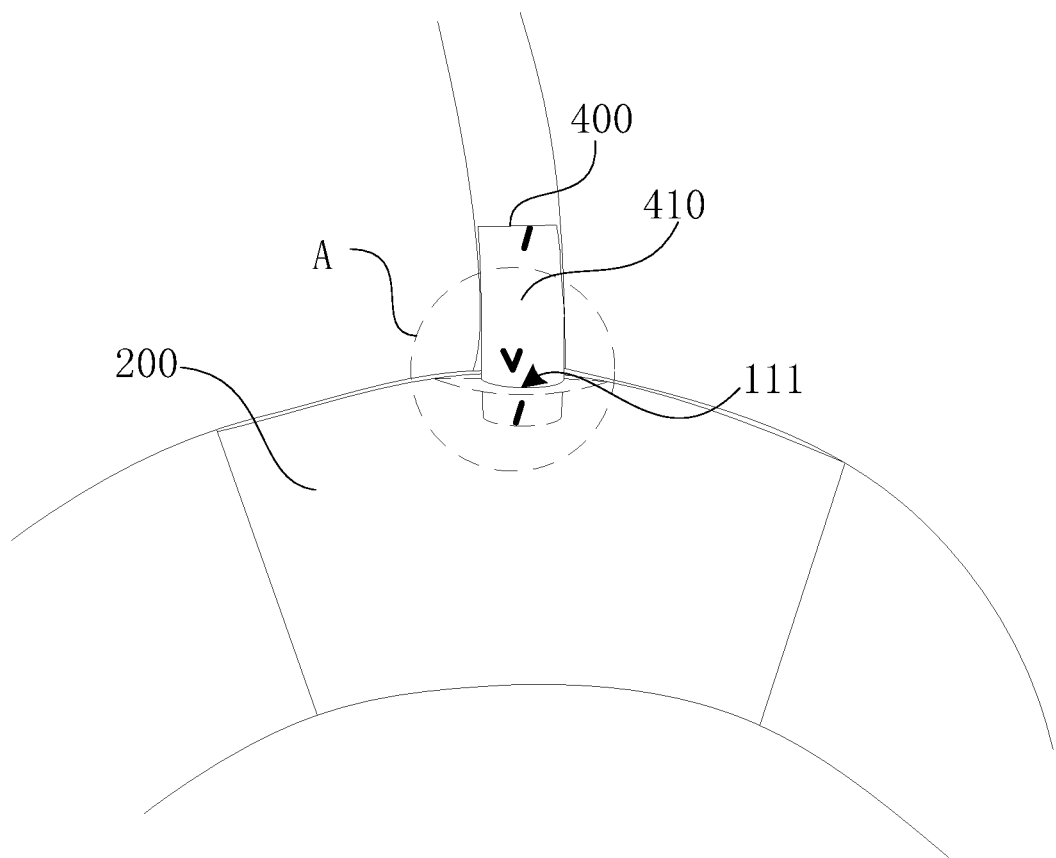
FIG. 8 is a schematic diagram showing a structure of the branch vessel stent as shown in FIG. 5 implanted into the main body stent.
Figure 9:
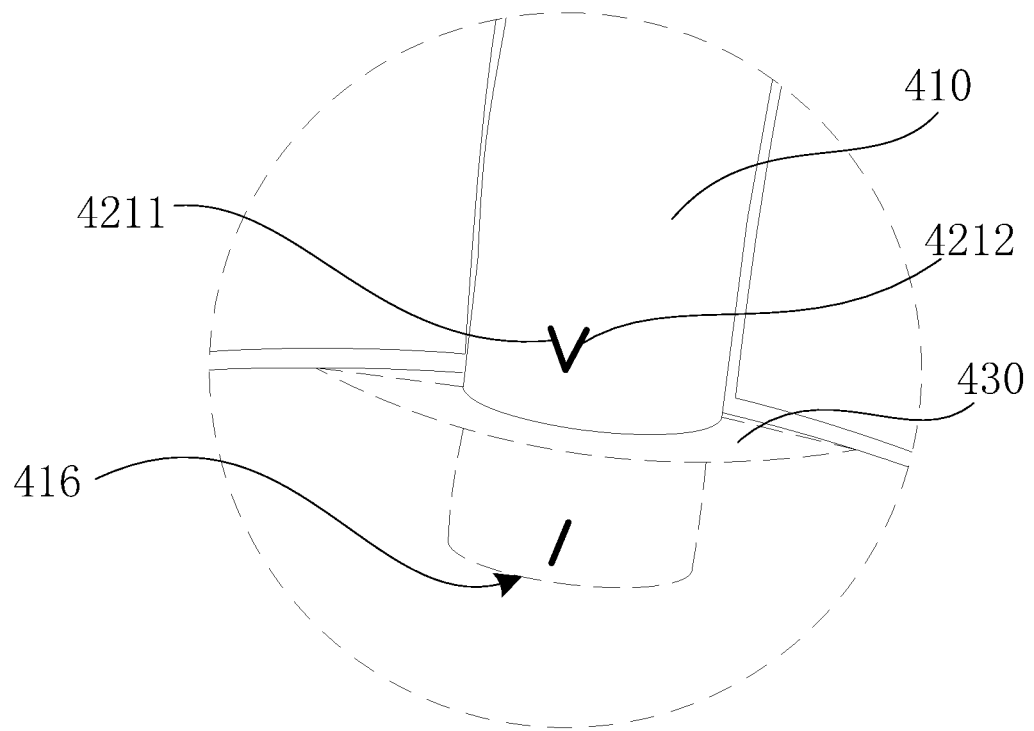
FIG. 9 is a schematic diagram showing the enlarged structure of the circled portion A in FIG. 8.

Referring together to FIGS. 8 and 9, during the operation, the main body stent 200 is first completely released at a lesion when the branch vessel stent 400 is used for vascular reconstruction, and in-situ fenestration is conducted to expand to the preset pore diameter via a fenestration instrument at a position where the main body stent 200 is located at an intersection 111 of the branch vessel; then the branch vessel stent 400 is inserted via a lumen of a sheath along the path of branch guide wire. During the implantation of the branch vessel stent 400, the first end 416 is a front end of the stent 400 for the branch vessel; the branch vessel stent 400 is implanted until the first developing portion 4211 and the second developing portion 4212 completely enter into the main body stent 200, finishing the initial positioning at this time; then the branch vessel stent 400 is released from the lumen until one end that is away from the first end 416 of the first developing portion 4211 or the second developing portion 4212, and the skirt-sided stent 430, is released; afterwards, a release device of the lumen is locked, and the lumen and the branch vessel stent 400 are pulled to move towards one end away from the main vessel of the branch vessel therein until the first developing portion 4211 and the second developing portion 4212 are flush with the wall of the intersection 111 at the position where the intersection thereof is on a plane perpendicular to the axial direction the stent body 410, with the pulling stopping at this time. Moreover, the flexible section 431 is squeezed to adhere to the inner wall of the main body stent 200, thus effectively blocking the position of the intersection 111; finally, the stent 400 for the branch vessel is completely released from the lumen of the sheath.

The various technical features of the above-mentioned embodiments may be combined in any way, and in order to simplify the description, not all possible combinations of the technical features of the above-mentioned embodiments are described, however, as long as there is no conflict between these technical features, they should be considered to be within the scope of the description.

The embodiments described above represent only a few embodiments of the present disclosure, the description of which is specific and detailed, but should not be construed to limit the scope of the present disclosure. It can be noted that several variations and modifications may be made by those skilled in the art without departing from the spirit of the present disclosure, which all fall within the scope of the present disclosure. Therefore, the protection scope of the patent for the present disclosure shall be determined by the appended claims.

The invention claimed is:

1. A branch vessel stent, comprising a stent body and a first developing member, wherein the stent body has an axial direction, is provided with a first end and a second end opposite to the first end, and comprises a bare stent; the first developing member is located between the first end and the second end, and close to the first end, and the first developing member comprises a first developing portion and a second developing portion, with each of the first developing portion and the second developing portion having a first end;
the first developing portion extends along a first direction, and the second developing portion extends along a second direction; the first direction obliquely intersects with the second direction; a length of the first developing portion and a length of the second developing portion in the axial direction of the stent body are both not less than 0.5 mm;
a distance between the intersection of the first developing portion and the second developing portion on a plane perpendicular to the axial direction of the stent body gradually increases from a position where the distance is the minimum distance to an end that is away from the first end of the first developing portion or the second developing portion; the minimum distance between the intersections of the first developing portion and the second developing portion on a plane perpendicular to the axial direction of the stent body is not greater than 2 mm;
wherein the bare stent comprises a plurality of axially arranged wave rings, and the wave rings comprise a plurality of alternately arranged wave crests and wave troughs, and the adjacent wave crests and the wave troughs are connected with each other by a wave rod; the first developing portion is arranged on the wave rod, and the second developing portion is arranged on a wave rod adjacent to the wave rod of a same wave ring where the first developing portion is located on; and
wherein the length of the first developing portion and the length of the second developing portion are both ½ to ⅔ of that of the corresponding wave rods.

2. A branch vessel stent, comprising a stent body and a first developing member, wherein the stent body has an axial direction, is provided with a first end and a second end opposite to the first end, and comprises a bare stent; the first developing member is located between the first end and the second end, and close to the first end, and the first developing member comprises a first developing portion and a second developing portion, with each of the first developing portion and the second developing portion having a first end;
the first developing portion extends along a first direction, and the second developing portion extends along a second direction; the first direction obliquely intersects with the second direction; a length of the first developing portion and a length of the second developing portion in the axial direction of the stent body are both not less than 0.5 mm;
a distance between the intersection of the first developing portion and the second developing portion on a plane perpendicular to the axial direction of the stent body gradually increases from a position where the distance is the minimum distance to an end that is away from the first end of the first developing portion or the second developing portion; the minimum distance between the intersections of the first developing portion and the second developing portion on a plane perpendicular to the axial direction of the stent body is not greater than 2 mm;
wherein the branch vessel stent further comprises a skirt-sided stent that surrounds the stent body, and the skirt-sided stent is connected to the stent body and extends toward the first end, and one end that is away from the first end and one end that is away from the first end of the first developing portion and the second developing portion is located at a joint portion of the skirt-sided stent and the stent body; and
wherein the skirt-sided stent comprises a flexible section and a folding section connected with the flexible section, and the flexible section is connected with the stent body; a distance from one end that is away from the first end of the first developing portion or the second developing portion, to the position where the distance between the intersections of the first developing portion and the second developing portion on the plane perpendicular to the axial direction of the stent body is the minimum distance, is equal to the length of a contour line of the flexible section.

* * * * *